US009717435B2

(12) United States Patent
Walker et al.

(10) Patent No.: US 9,717,435 B2
(45) Date of Patent: Aug. 1, 2017

(54) INTRAVENOUS LINE FLOW SENSOR FOR ADVANCED DIAGNOSTICS AND MONITORING IN EMERGENCY MEDICINE

(71) Applicant: Physio-Control, Inc., Redmond, WA (US)

(72) Inventors: Robert G. Walker, Seattle, WA (US); Barry D. Curtin, Seattle, WA (US)

(73) Assignee: Physio-Control, Inc., Redmond, WA (US)

( * ) Notice: Subject to any disclaimer, the term of this patent is extended or adjusted under 35 U.S.C. 154(b) by 0 days.

(21) Appl. No.: 14/738,795

(22) Filed: Jun. 12, 2015

(65) Prior Publication Data

US 2015/0359964 A1 Dec. 17, 2015

Related U.S. Application Data

(60) Provisional application No. 62/012,055, filed on Jun. 13, 2014.

(51) Int. Cl.
| | |
|---|---|
| *A61B 5/044* | (2006.01) |
| *A61N 1/04* | (2006.01) |
| *A61B 5/046* | (2006.01) |
| *A61N 1/39* | (2006.01) |
| *A61B 5/0428* | (2006.01) |
| *A61M 5/168* | (2006.01) |

(52) U.S. Cl.
CPC .............. *A61B 5/044* (2013.01); *A61B 5/046* (2013.01); *A61M 5/16831* (2013.01); *A61N 1/046* (2013.01); *A61N 1/3937* (2013.01); *A61B 5/04286* (2013.01); *A61M 2005/16863* (2013.01); *A61M 2205/18* (2013.01); *A61M 2205/3334* (2013.01); *A61M 2205/3375* (2013.01); *A61N 1/3993* (2013.01)

(58) Field of Classification Search
CPC ........ A61N 1/046; A61N 1/056; A61N 1/139; A61B 2018/00744; A61B 5/02; A61B 5/026; A61B 5/145; A61B 8/06
See application file for complete search history.

(56) References Cited

U.S. PATENT DOCUMENTS

| | | | | |
|---|---|---|---|---|
| 4,834,100 A | * | 5/1989 | Charms | ................ A61N 1/3956 607/2 |
| 2002/0173725 A1 | * | 11/2002 | Rock | ...................... A61B 5/061 600/500 |
| 2003/0077943 A1 | * | 4/2003 | Osypka | .................. A61N 1/056 439/623 |
| 2007/0219480 A1 | * | 9/2007 | Kamen | .................. G01F 22/00 604/20 |

(Continued)

*Primary Examiner* — Edward Moran
*Assistant Examiner* — Natasha Patel
(74) *Attorney, Agent, or Firm* — Lane Powell PC

(57) ABSTRACT

A portable medical device having an intravenous line flow sensor integrated into a cable. The portable medical device may be a defibrillator having an ECG or electrode cable couple to ECG or electrode leads. The flow sensor may be integrated into the ECG or electrode cable. The portable medical device uses the flow sensor to capture and store information about fluids delivered to a patient being treated with the portable medical device. The information may include total volume provided, flow rate, and the like. The information may then be used to evaluate the treatment provided to the patient.

15 Claims, 5 Drawing Sheets

(56) References Cited

U.S. PATENT DOCUMENTS

2007/0238939 A1* 10/2007 Giftakis ............... A61B 5/0402
                                                      600/301
2012/0191476 A1*  7/2012 Reid .................... G06Q 50/24
                                                      705/3

* cited by examiner

DEFIBRILLATION SCENE

| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |

TWO MAIN TYPES OF EXTERNAL DEFIBRILLATORS

COMPONENTS OF EXTERNAL DEFIBRILLATOR

INTRAVENOUS LINE FLOW SENSOR FOR ADVANCED DIAGNOSTICS AND MONITORING IN EMERGENCY MEDICINE

CROSS REFERENCE TO RELATED APPLICATIONS

This patent application claims the benefit of and priority to U.S. Provisional Patent Application Ser. No. 62/012,055 filed on Jun. 13, 2014, entitled "Intravenous Line Flow Sensor Integrated Into ECG Cable," the disclosure of which is hereby incorporated by reference for all purposes.

TECHNICAL FIELD

The disclosed subject matter pertains generally to the area of medical devices, and more specifically to the area of portable monitoring or monitor/defibrillator.

BACKGROUND INFORMATION

Intravenous and intraosseous (generically referred to as "IV") access and fluid delivery are components of many types of EMS and emergency medicine patient care events. IV fluids are given for many different reasons, such as resuscitation, temperature management, hydration, correction of metabolic/electrolytic disturbances, as a vehicle for administration of pharmacologic agents, and the like. In most of these uses, there is a target fluid volume and/or instantaneous flow rate that is considered "best practice." In some cases, delivery of larger or smaller than accurate volumes or rates may have detrimental effects for the patient.

In some clinical settings, such as pre-hospital emergency care, existing documentation and quality assurance practices regarding IV fluid volumes are minimal and imprecise. For example, even in many pre-hospital research studies related to fluid resuscitation, where administered fluid volume is a critical variable or even the intervention of interest, volumes are crudely estimated after the fact by counting the number of completely or partially used fluid bags. Inaccuracy can thus result from both the lack of a precise means of measurement, and delays to manual documentation of the data.

Setting an accurate drip rate on an IV line, particularly during patient transport, can be challenging. Additionally, the person setting the drip may not be the person ordering the fluid delivery parameters, and they may therefore not fully appreciate the possible harmful sequelae associated with incorrect fluid flows or volumes.

A practical method to more accurately monitor IV fluid flow rates and delivered volumes applicable to the unique user and use environment needs of pre-hospital care and transport has eluded those skilled in the art, until now.

SUMMARY OF EMBODIMENTS

Certain embodiments are directed to a medical apparatus, such as a defibrillator having a cable providing connectivity between the defibrillator and at least one of a defibrillation electrode or an ECG monitoring electrode, the defibrillator being operative to deliver a defibrillation shock through the defibrillation electrode and monitor the ECG through either the defibrillation electrode or the ECG monitoring electrode; and a flow sensor coupled to the cable, the flow sensor being operative to detect a flow of fluids through an intravenous line.

Other embodiments are directed to a medical apparatus, such as a portable monitor having a plurality of sensors for diagnostics and monitoring. The portable monitor having an integrated flow sensor and being configured to monitor, display, and record a volume of fluid delivered to the patient through an intravenous line.

In many instances portable monitors and defibrillators are combined to provide a single device with advanced diagnostics, monitoring, and therapy.

BRIEF DESCRIPTION OF THE DRAWINGS

FIG. 1 is a diagram of a scene where an external defibrillator is used to try and save the life of a person in accordance with an embodiment.

FIG. 2 is a table listing two main types of the external defibrillator shown in FIG. 1, and who they might be used by.

DETAILED DESCRIPTION

Generally described, the disclosure is directed to a flow sensor that can be used to monitor intravenous delivery of fluids.

Description of Operative Environment for Embodiments

Figures 1, 2:
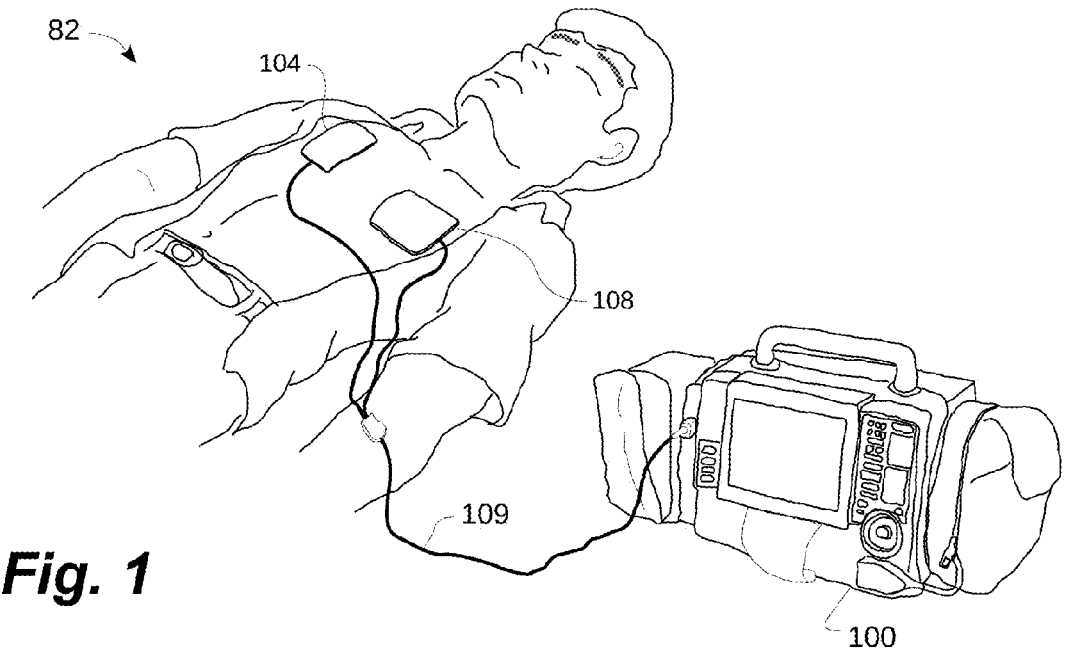

FIG. 1 is a diagram of a defibrillation scene. A person 82 is lying supine. Person 82 could be a patient in a hospital or someone found unconscious. Person 82 is experiencing a medical emergency, which could be, by way of an example, Ventricular Fibrillation (VF).

A portable external defibrillator 100 has been brought close to person 82. The portable external defibrillator can also be a hybrid monitor/defibrillator. At least two defibrillation electrodes 104, 108 are usually provided with external defibrillator 100. Electrodes 104, 108 are coupled with external defibrillator 100 via electrode leads 109. A rescuer (not shown) has attached electrodes 104, 108 to the skin of person 82. Defibrillator 100 is monitoring cardiac rhythms and potentially administering, via electrodes 104, 108, a brief, strong electric pulse through the body of person 82. The pulse, also known as a defibrillation shock, goes through the person's heart in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

FIG. 2 is a table listing examples of types of external defibrillators and their primary intended users. A first type of defibrillator 100 is generally called a defibrillator-monitor (or monitor-defibrillator) because it is typically formed as a single unit in combination with a patient monitor. Alternatively, the defibrillator-monitor may be a modular device with separable components. For example, in one alternative embodiment, the defibrillator-monitor may include a base component and a plurality of detachable pods. Each pod communicates with the base component, perhaps wirelessly. Certain pods may be used to collect information about a patient, such as vital statistics. One example of such an alternative system is described in U.S. Pat. No. 8,738,128 entitled "Defibrillator/Monitor System Having A Pod With Leads Capable Of Wirelessly Communicating," the disclosure of which is hereby incorporated by reference for all purposes. A defibrillator-monitor is intended to be used by medical professionals, such as doctors, nurses, paramedics, emergency medical technicians, etc. Such a defibrillator-monitor is generally intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals, such as a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator." An AED typically makes the shock/no shock determination by itself, automatically. It can typically sense enough physiological conditions of the person 82 using only the defibrillation electrodes 104, 108 shown in FIG. 1. An AED can either administer the shock automatically, or instruct the user to do so, e.g. by pushing a button.

There are other types of external defibrillators in addition to those listed in FIG. 2. For example, a hybrid defibrillator can have aspects of an AED and also of a defibrillator-monitor. A usual such aspect is additional ECG monitoring capability.

Figure 3:
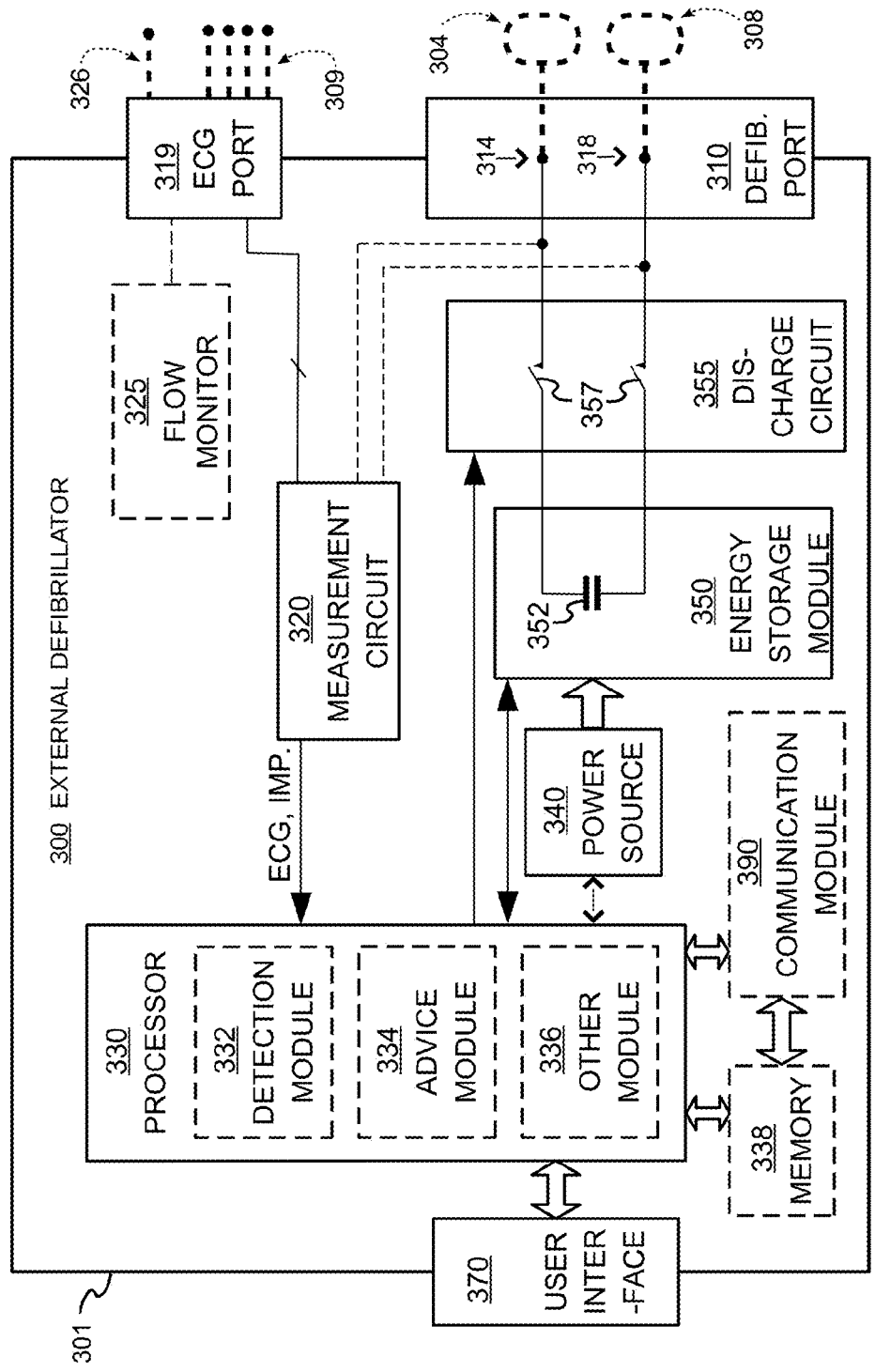
FIG. 3 is a diagram showing components of an external defibrillator made according to embodiments.

FIG. 3 is a diagram showing components of an external defibrillator 300 made according to embodiments. These components can be, for example, in external defibrillator 100 of FIG. 1. Plus, the components shown in FIG. 3 can be provided in a housing 301, also known as a casing.

External defibrillator 300 is intended for use by a user, who would be the rescuer. Defibrillator 300 typically includes a defibrillation port 310, such as a socket in housing 301. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding an electrical charge to person 82 via electrodes 304, 308. The electrical charge may be stored in defibrillator 300, as discussed below.

If defibrillator 300 is a defibrillator-monitor, as was described with reference to FIG. 2, it will frequently also have an ECG port 319 in housing 301, for plugging in ECG lead wires 309. ECG lead wires 309 can sense an ECG signal, such as any of the ECG lead signals that comprise a common 12-lead ECG recording. Other types of ECG lead signals are equally applicable. A defibrillator-monitor could have additional ports that are not shown.

In one embodiment, the defibrillator 300 may include a flow monitor component 325 coupled to a flow sensor lead 326, which may be integrated into the ECG port 319. In one specific implementation, the flow monitor component 325 may includes functions and operations to monitor, via a flow sensor (not shown), the volume and rate of flow of fluids being delivered to a patient using an intravenous line. Although shown as integrated within the ECG port 319, alternative embodiments may use a separate port for the flow sensor lead 326 or integrate the flow sensor lead 326 into a different port, such as the defibrillation port 310.

Defibrillator 300 also includes a measurement circuit 320. Measurement circuit 320 receives physiological signals from ECG port 319, and also from other ports, if provided. These physiological signals are sensed, and information about them is rendered by measurement circuit 320 as data, or other signals, etc.

Defibrillator 300 also includes a processor 330, which may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions too numerous to list here. In addition, if flow monitor component 325 is provided, it may be implemented as a module executing, at least in part, within processor 330.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. In addition, memory 338 can store prompts for the user, etc. Moreover, memory 338 can store patient data, such as, for example, data regarding how much fluid may have been administered to patient 82 as detected by the flow monitor component 325.

Defibrillator 300 may also include a power source 340. To enable portability of defibrillator 300, power source 340 typically includes a battery. Such a battery is typically implemented as a battery pack, which can be rechargeable or not. Sometimes, a combination of rechargeable and non-rechargeable battery packs is used. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, or the like.

Defibrillator 300 moreover includes a discharge circuit 355. Discharge circuit 355 can be controlled to permit the energy stored in module 350 to be discharged to nodes 314, 318, and thus also to defibrillation electrodes 304, 308. Discharge circuit 355 can include one or more switches 357. Those can be made in a number of ways, such as by an H-bridge, or the like.

Defibrillator 300 further includes a user interface 370. User interface 370 can be made in any number of ways. For example, interface 370 may include a screen, to display what is detected and measured, provide visual feedback to a rescuer for their resuscitation attempts, and so on. User interface 370 may also include a speaker to issue audible signals, such as voice prompts, or the like. The user interface 370 may issue prompts to the user, visually or audibly, so that the user can administer CPR, for example. Interface 370 may additionally include various controls, such as pushbuttons, keyboards, touch screens, and so on. In addition, discharge circuit 355 can be controlled by processor 330, or directly by user via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

Embodiments of a Defibrillator with Integrated Flow Sensor

Figure 4:
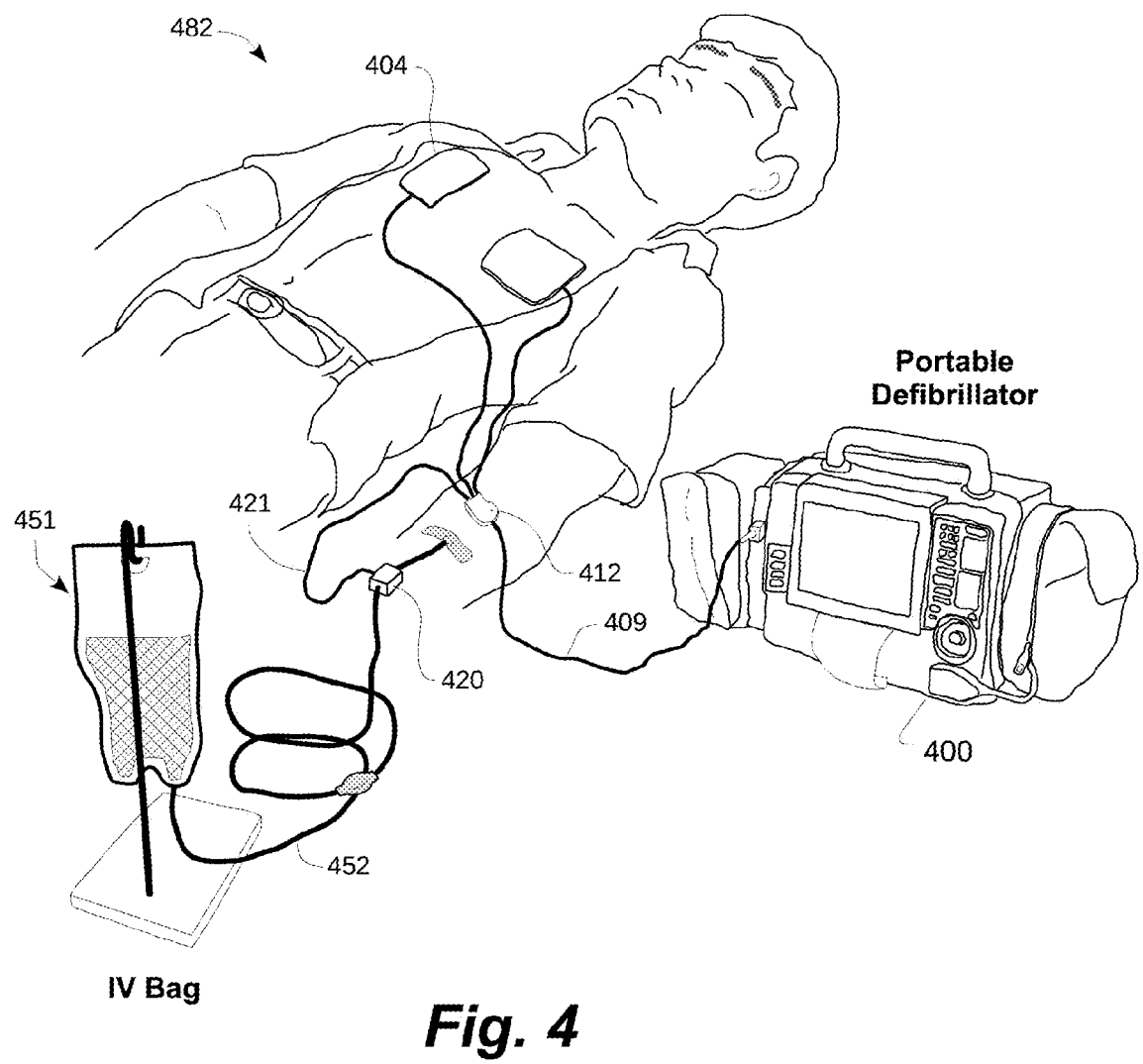
FIG. 4 is a diagram generally illustrating a scene where an external defibrillator is used on a person while fluids are being delivered to the person through an intravenous line.

FIG. 4 is a representation of a defibrillation scene at which a patient 482 is experiencing a medical emergency, such as ventricular fibrillation. The patient 482 may also be exhibiting other symptoms, which prompt a rescuer to administer fluids 451 via an intravenous line 452. The intravenous line 452 is attached to or inserted into the patient 482, in this instance, in the patient's arm.

Because he is exhibiting symptoms of ventricular fibrillation, a rescuer has attached a portable external defibrillator (Device 400) to the patient 482. Device 400 is connected to patient 482 using electrode leads 409 coupled to electrodes, such as electrode 404, attached to the patient 482. For simplicity of illustration and discussion, electrode leads 409 are shown as a single cable connecting directly to electrodes attached to the patient 482. However, those skilled in the art will appreciate that in some embodiments, there may be two or more wire harnesses. For example, there may be one wire harness that includes electrode leads, and another wire harness that attaches to ECG monitoring patches. In still other embodiments, the electrodes used to deliver a defibrillation shock may also function to monitor the heart rhythm of the patient 482 while not being used to deliver the defibrillation shock. In such an embodiment, a single wire harness may serve as both the electrode leads and the ECG leads. For the sake of simplicity only, a single wire harness that includes the electrode leads 409 will be discussed. However, the instant teachings are equally applicable to other configurations.

In the disclosed embodiments, a flow sensor 420 is used to monitor the flow characteristics (e.g., volume, rate, etc.) of the fluids 451 being intravenously delivered to the patient 482. The flow sensor 420 can take various different forms. For instance, the flow sensor could be based on ultrasound measurement techniques, such as, e.g., Doppler ultrasound. Alternatively, the flow sensor could incorporate optical sensing capabilities, which could be used to, for example, detect air/gas bubbles in the fluid within the IV line. Such flow sensor technology could be physically optimized and incorporated into an ECG cable wire or electrode connector. In yet another alternative, optical (e.g., laser Doppler), photo-acoustic Doppler, or thermal flow detection technologies could be employed in other embodiments. Still further, the flow sensor could employ any other technology acceptable for sensing fluid flow.

Figure 5:
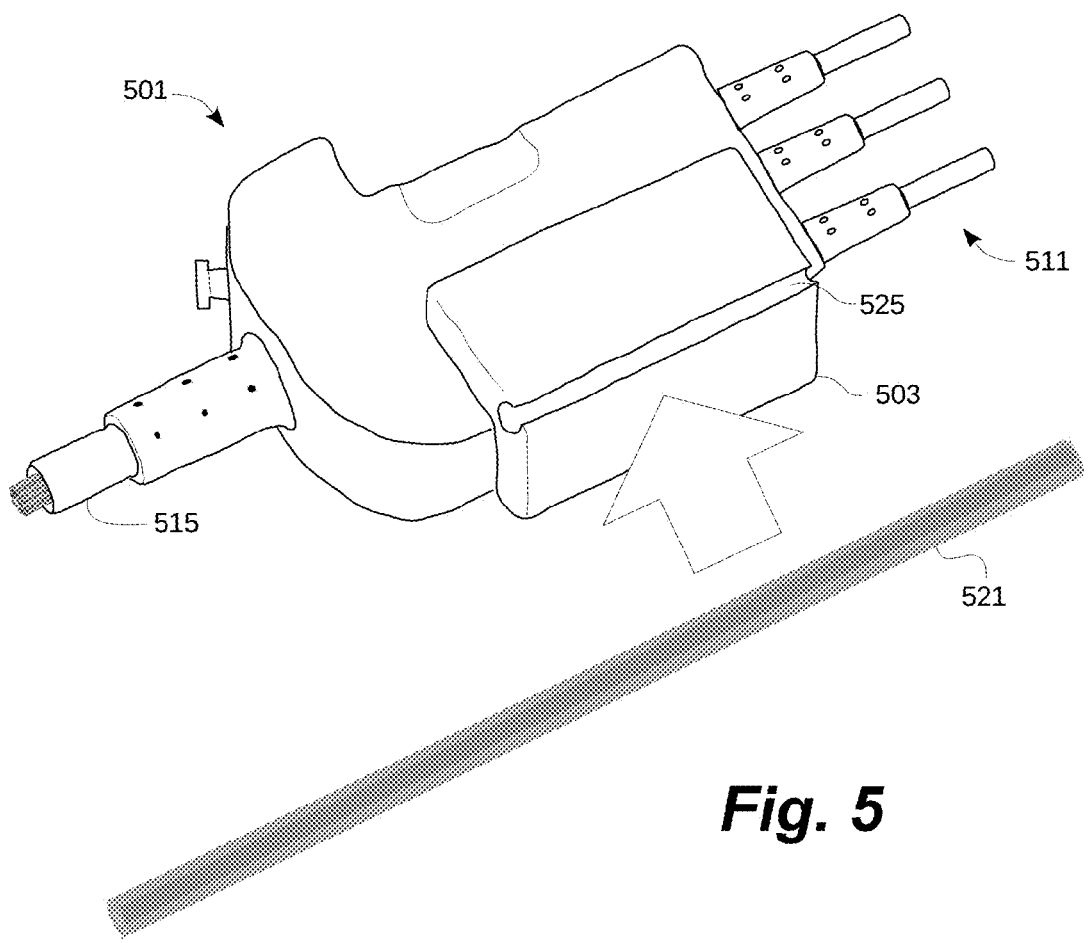
FIG. 5 is a conceptual illustration of a cable yoke with an integrated flow sensor, in accordance with one embodiment.
Figure 6:
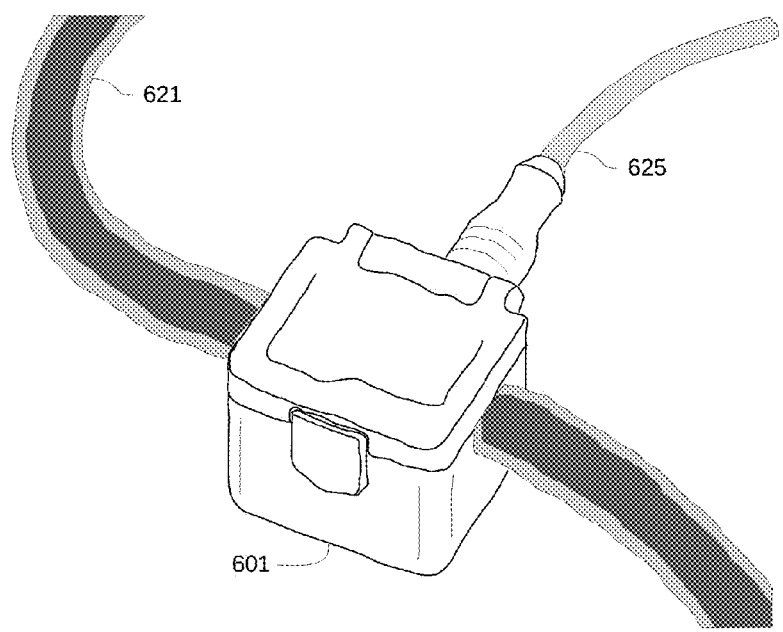
FIG. 6 is a conceptual diagram of an integrated flow sensor for use with a defibrillator, in accordance with another embodiment.

In this particular embodiment, the flow sensor 420 is shown as a separate device coupled to an ECG wiring harness yoke 412 with a flow sensor lead 421. Other embodiments may take many different forms. For example, a small flow sensor may be physically incorporated into either a node along an ECG lead wire, or the housing of one of the standard ECG electrode snap connectors (e.g., the left arm and/or right arm ECG wire or electrode connector). Specific exemplary, non-limiting embodiments are illustrated in FIGS. 5 and 6, and described below.

Described briefly here, the flow sensor 420 accepts an intravenous line 452 so that Device 400 may monitor the flow characteristics of the intravenous line 452. Making use of the flow sensor 420, the AED 400 collects and monitors information about how much fluid is being delivered or was delivered to the patient 482. For example, Device 400 outfitted with the flow sensor 420 may perform any one or more of the following illustrative functions:

(1) Display and record instantaneous flow rate;
(2) Detect and alert to flow stoppage conditions, which if not intentional, could indicate an issue needing attention, such as a kinked intravenous line 452, clotted cannula, empty bag 451, or the like;
(3) Detect and alert to situations (e.g. empty bag) with retrograde flow of blood back into the IV line;
(4) Monitor, display, and record cumulative fluid volume; and
(5) Conduct real-time smart surveillance of data from the flow sensor 420, integrating logic tied to patient-condition-specific protocols and treatments.

In still other embodiments, the AED 400 incorporating the flow sensor 420 can use patient and/or protocol information derived from other monitor data, or via wireless connectivity to an electronic patient care reporting (ePCR) or other medical data system, to identify mismatches between expected and observed fluid therapy, and provide an appropriate user alert. For example, if the documented patient complaint/assessment/etc is one where standard pre-hospital treatment protocols would call for setting an slow IV drip rate (or there is real-time documentation in the ePCR that the IV drip is set to a slow rate), and the flow sensor 420 detects that fluids are being delivered at a faster rate, an alert such as "check IV drip rate" could be provided. Even further, guidance on the expected drip rate for the condition could also be provided.

In addition to recording the above data for documentation and post-event QA/QI purposes, an algorithm is disclosed that identifies sharp and transient increases or perturbations to the flow rate, which would typically be indicative of injection of a medication into the line 452. Embodiments could thus be used to automatically and accurately identify and record the timing of administration of medications. The sensor could also detect and alert/record an excessive amount of air (bubbles) moving through the intravenous line 452.

In alternative embodiments, the flow sensor 420 could be combined with a fluid temperature sensor, such as a thermocouple, to calculate and document effective cooling power when cold IV fluids are used to initiate therapeutic hypothermia.

FIG. 5 is a conceptual illustration of a cable yoke 501 with an integrated flow sensor 503. In this embodiment, the cable yoke 501 receives an ECG cable 515 from a defibrillator, such as AED 400. The cable yoke 501 outputs a number of ECG leads 511 that each feed an ECG patch (not shown) affixed to a patient to monitor the heart rhythm of the patient. Common such systems include between 3 and 10 ECG leads 511. In this particular implementation, the flow sensor 503 is integrated directly into the ECG cable yoke 501, which eliminates the need for any separate hardware or components.

Also shown in FIG. 5 is an intravenous line 521 that may be connected to a patient. In situations where both a defibrillator and an IV are connected to a patient, the left arm or right arm ECG wires are normally placed in a location reasonably adjacent to the IV line. This proximity of the IV line 521 to the ECG cable yoke 501 makes attachment of the IV line 521 to the flow sensor 503 simple and not problematic from an entanglement or motion constraint standpoint. In this particular embodiment, the IV line 521 is inserted into an opening 525 in the flow sensor 503 configured to securely contain the IV line 521. In use, after establishing IV access and connecting the IV line 521 to an IV port on the patient, the IV line 521 would be "snapped" into the opening 525 of the flow sensor 503 on the nearest ECG wire/connector. The monitor could then automatically begin monitoring, displaying, and alerting as appropriate regarding the instantaneous flow and cumulative fluid volume.

FIG. 6 is a conceptual diagram of another implementation of an integrated flow sensor 601 for use with a defibrillator. In this embodiment, the flow sensor 601 is not directly integrated into an ECG cable, but rather, is a free-standing component that is connected to the ECG cable by a flow sensor lead 625 that is connected to the ECG cable. As will be apparent to those skilled in the art, the flow sensor lead 625 could alternatively be connected to an electrode lead or cable, or yet another component of a defibrillator. In this particular embodiment, the flow sensor 601 may be positioned proximate to an IV line 621. The IV line 621 may then be snapped into the flow sensor 601. This particular implementation provides greater flexibility for connecting to an IV line 621 without placing any unnecessary burdens or requirements on the positioning of the IV line 621. In this way, the embodiment shown in FIG. 6 provides certain advantages over the embodiment shown in FIG. 5. However, having an additional wire and component protruding from the defibrillator may make the embodiment shown in FIG. 5 preferable.

Thus the preferred embodiment of sensor integration into a monitor/defibrillator system involves physical incorporation of the flow sensor into an element of a monitoring cable (e.g. housing of an electrode snap connector, a node along the ECG cable or an electrode wire, in the cable yoke, or the like). Still other alternative embodiments could include physical incorporation of the flow sensor into the main body of a monitor/defibrillator, or into a detachable pod that provides monitoring connections closer to the patient. The sensor could also exist as a standalone unit, wirelessly connected to the monitor/defibrillator.

Many other embodiments are possible, subject to some guiding principles. for example, embodiments preferably do not require additional cabling to connect the flow sensor to the patient or IV line. In addition, other alternative embodiments preferably are not standalone wireless units, because such units would likely frequently be forgotten in the commotion of the moment, and either accidentally disposed of along with the disposable IV line and bag, or accidentally left with the patient upon hand-off to the ED, leading to excessive equipment loss.

Embodiments can have advantages over other technologies in many ways. For example, embodiments enable easier and more accurate real-time control of the proper target rate/volume for IV delivered fluids. In addition, embodiments facilitate real-time alerts to fluid volume/flow "error conditions" (e.g. "line occluded", "bag empty with retrograde flow of blood back into the line", "inappropriate flow rate or cumulative volume for patient condition", etc.). Still further, embodiments can capture additional data to facilitate more detailed and accurate reconstruction of the patient care event for post-event QA/QI purposes.

Other embodiments may include combinations and sub-combinations of features described or shown in FIGS. 3-6, including for example, embodiments that are equivalent to providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, "feature" or "features" can refer to structures and/or functions of an apparatus, article of manufacture or system, and/or the steps, acts, or modalities of a method.

In the foregoing description, numerous details have been set forth in order to provide a sufficient understanding of the described embodiments. In other instances, well-known features have been omitted or simplified to not unnecessarily obscure the description.

A person skilled in the art in view of this description will be able to practice the disclosed invention. The specific embodiments disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems. The following claims define certain combinations and subcombinations of elements, features, steps, and/or functions, which are regarded as novel and non-obvious.

Additional claims for other combinations and subcombinations may be presented in this or a related document.

What is claimed is:

1. A medical apparatus, comprising:
   a portable monitor having a defibrillator component, the monitor having a cable providing connectivity between the monitor and an electrode positioned non-transvenously the defibrillator component being operative to deliver a defibrillation shock through the electrode; and
   a flow sensor coupled to the defibrillator component, the flow sensor being operative to detect a flow of a fluid through an intravenous line;
   wherein the portable monitor is configured to analyze the flow and to output for display information based on the flow.

2. The medical apparatus recited in claim 1, wherein the defibrillator component is detachable from the portable monitor.

3. The medical apparatus recited in claim 2, wherein the defibrillator component and a monitor display component are each separable from a monitor connections component of the portable monitor.

4. The medical apparatus recited in claim 1, wherein the portable monitor comprises a flow meter component configured to monitor the flow of a fluid through the intravenous line.

5. The medical apparatus recited in claim 1, wherein the flow sensor comprises an ultrasound-based flow sensor.

6. The medical apparatus recited in claim 1, wherein the electrode comprises a defibrillation electrode that is integrated with an ECG monitoring electrode into a unitary component.

7. The medical apparatus recited in claim 1, wherein the flow sensor is integrated into a yoke portion of the cable, the yoke portion operating to split the cable into a plurality of separate ECG lead wires, each ECG lead wire connecting to a different ECG monitoring electrode.

8. The medical apparatus recited in claim 1, wherein the flow sensor is separate from the cable and joined to the cable by a flow sensor lead.

9. A medical apparatus, comprising:
   a portable defibrillator to which a plurality of electrodes may be attached, the defibrillator being configured to deliver a defibrillation shock to a patient through the plurality of electrodes;
   the portable defibrillator further having an integrated flow sensor, the defibrillator being further configured to monitor, display, and record a volume of fluid delivered to the patient through an intravenous line.

10. The medical apparatus recited in claim 9, wherein the portable defibrillator is further configured to detect that the intravenous line is in a flow stoppage condition, and to issue an alert to the flow stoppage condition.

11. The medical apparatus recited in claim 9, wherein the portable defibrillator is further configured to detect to a retrograde flow situation in which blood is flowing back into the intravenous line, and to issue an alert to the retrograde flow situation.

12. The medical apparatus recited in claim 9, wherein the portable defibrillator is further configured to conduct substantially real-time surveillance of data from the flow sensor.

13. The medical apparatus recited in claim 12, wherein the portable defibrillator is still further configured to perform analysis of the substantially real-time surveillance combined with patient-condition-specific data to issue feedback on the volume of fluid delivered to the patient through the intravenous line.

14. The medical apparatus recited in claim 9, wherein the portable defibrillator is detachable from a portable monitor.

15. The medical apparatus recited in claim 9, wherein the flow sensor comprises an ultrasound-based flow sensor.

* * * * *

UNITED STATES PATENT AND TRADEMARK OFFICE
CERTIFICATE OF CORRECTION

PATENT NO. : 9,717,435 B2
APPLICATION NO. : 14/738795
DATED : August 1, 2017
INVENTOR(S) : Robert G. Walker and Barry D. Curtin It is certified that error appears in the above-identified patent and that said Letters Patent is hereby corrected as shown below:

In the Claims

Claim 9, Line 9, reads: "the portable defibrillator further having an integrated flow;" should read "the medical apparatus further having an integrated flow"

Claim 9, Line 10, reads: "sensor, the defibrillator being further configured to;" should read "sensor, the medical apparatus being further configured to"

Signed and Sealed this
Fourteenth Day of November, 2017

Joseph Matal
*Performing the Functions and Duties of the
Under Secretary of Commerce for Intellectual Property and
Director of the United States Patent and Trademark Office*